United States Patent [19]

Choudhary et al.

[11] Patent Number: 6,020,534
[45] Date of Patent: Feb. 1, 2000

[54] PROCESS FOR PRODUCTION OF PROPYLENE AND ETHYLENE BY NON-CATALYTIC OXYCRACKING OF PROPANE OR PROPANE-RICH $C_2$-$C_4$ PARAFFINS

[75] Inventors: Vasant Ramchandra Choudhary; Amarjeet Munshiram Rajput; Vilas Hari Rane, all of Maharashtra, India

[73] Assignee: Council of Scientific Research, New Delhi, India

[ * ] Notice: This patent is subject to a terminal disclaimer.

[21] Appl. No.: 09/141,685

[22] Filed: Aug. 28, 1998

[30] Foreign Application Priority Data

Jun. 26, 1998 [IN] India ................................ 1770/Del/98

[51] Int. Cl.[7] ................................ C07C 4/02; C07C 5/09
[52] U.S. Cl. .......................... 585/652; 585/648; 585/650; 585/621; 585/910
[58] Field of Search .................................... 585/652, 650, 585/648, 621, 910

[56] References Cited

U.S. PATENT DOCUMENTS

| | | | |
|---|---|---|---|
| 4,426,278 | 1/1984 | Kosters | 585/652 |
| 5,306,854 | 4/1994 | Choudhary et al. | 585/315 |
| 5,463,159 | 10/1995 | Callejas et al. | 585/652 |
| 5,616,236 | 4/1997 | Brown et al. | 585/648 |
| 5,763,725 | 6/1998 | Choudhary et al. | 585/652 |
| 5,777,188 | 7/1998 | Reed et al. | 585/648 |
| 5,849,176 | 12/1998 | Zimmermann et al. | 585/648 |

*Primary Examiner*—Walter D. Griffin
*Assistant Examiner*—In Suk Bullock
*Attorney, Agent, or Firm*—Renner, Otto, Boisselle & Sklar, P.L.L.

[57] ABSTRACT

A process for the production of propylene and ethylene by non-catalytic oxidative conversion of propane by allowing the endothermic hydrocarbon cracking reaction to occur simultaneously with the exothermic hydrocarbons oxidative conversion reactions in an empty tubular reactor is disclosed. The process comprises mixing of oxygen and propane at ambient temperatures, mixing of sulfur compound with steam, admixing the mixture of steam and sulfur compound and the mixture of oxygen and propane and preheating the resulting admixture, passing said mixture through an empty tubular reactor, cooling and separating the components of effluent product gases by known methods and recycling the unconverted reactants, if required.

6 Claims, No Drawings

PROCESS FOR PRODUCTION OF PROPYLENE AND ETHYLENE BY NON-CATALYTIC OXYCRACKING OF PROPANE OR PROPANE-RICH $C_2$-$C_4$ PARAFFINS

FIELD OF INVENTION

This invention relates to a process for the production of propylene and ethylene by non-catalytic oxidative cracking of propane or propane-rich $C_2$–$C_4$ paraffins. The invention particularly relates to production of propylene and ethylene by non-catalytic oxidative conversion of propane or propane-rich $C_2$–$C_4$ paraffins in a most energy efficient manner by allowing the endothermic hydrocarbon cracking reactions to occur simultaneously with the exothermic hydrocarbons oxidative conversion reactions in an empty tubular reactor.

The process of this invention could be used for the production of propylene from propane or propane-rich $C_2$–$C_4$ paraffins.

BACKGROUND OF INVENTION

Propylene, an important feedstock in the petrochemical industry, is produced commercially along with ethylene by the thermal cracking of ethane, propane, ethane-propane mixture or naphtha in the presence of steam (ref. L. Kniel et al., in Chemical Industries, Vol. 2 "Ethylene: Key-stone to the Petrochemical Industry, Marcel Dekkor, Inc., New York, 1980 and L. F. Albright et al., eds., in Pyrolysis: Theory and Industrial Practice, Academic Press, New York, 1983). In the thermal cracking of these paraffins, ethylene is produced in larger quantities than propylene. The cracking process is highly endothermic and hence highly energy intensive and also involves extensive coke formation. Typical results given in the above references indicate that at 93% conversion of propane, 23.7 wt %, 41.4 wt % and 12.9 wt % yield for methane, ethylene and propylene, respectively, could be obtained by the thermal cracking of propane. The ethylene, propylene and also other olefins produced in the cracking process and the unreacted paraffins are separated from the product stream by the well-known cryogenic separation method involving liquefaction and fractionation of hydrocarbons.

The process for the production of propylene and ethylene, based on thermal cracking of propane or other paraffins have following limitations: (1) They are highly endothermic and hence require a large amount of energy for the cracking of paraffins. (2) They involve extensive coke deposition inside the pyrolysis reactor tubes, thus causing increase in pressure drop and hence there are frequent break-downs for removing the coke from the pyrolysis reactor tubes. (3) The life of the pyrolysis reactor tubes is low because of their high temperature operation; the temperature at external surface of the tubes is about 200° C. higher than the temperature inside the tubes.

Catalytic processes based on oxidative dehydrogenation of propane for the productions of propylene area also known in the prior art. A number of catalysts are known for the oxidative dehydrogenation of propane [ref. JP 58,153,538 (matushi Electric Ind. Co. Ltd.), 1983; U.S. Pat. No. 4,472,314, Conner et al., 1984; U.S. Pat. No. 4,547,618 (Mobil Oil Corp.), Porbus and Nancy, 1985; U.S. Pat. No. 4,607,129 (Phillips Petroleum Col.), Lee and Fu, 1985; U.S. Pat. No. 4,886,928, Imai and Schmidt, 1989; U.S. Pat. No. 5,306,858, Salem et al., 1994; JP 08,231,441, Saito et al., 1996 and DE 19,530,454, Baerns et al., 1997]. In the catalytic oxidative propane dehydrogenation processes, the catalyst is deactivated during the process due to the loss of active components from the catalyst by evaporation at hot spots and/or due to the catalyst sintering. The catalysts are also deactivated due to coke deposition on their surface during the process. Moreover, since these processes are highly exothermic, their operation is hazardous.

The present energy crisis and/or high energy cost, and also the environmental pollution problems have created a great need for developing a process for the production of propylene, the demand of which is increasing day-by-day, by non-catalytic oxidative cracking of propane or propane-rich $C_2$–$C_4$ paraffins to propylene and ethylene with high propylene/ethylene mole ratio, which requires little (i.e. much smaller than that required for the thermal cracking process) or no external energy, operates in a most energy efficient manner and with high conversion, selectivity and productivity but without coke formation and also has absolutely no hazards (i.e. very safe operation). This invention is, therefore, made with the following objects so that most of the drawbacks or limitations of the earlier processes could be overcome.

OBJECTS OF THE INVENTION

1. Accordingly the main object of this invention is to provide process for the production of propylene and ethylene, with propylene/ethylene mole ratio of at least 0.15, from propane or propane-rich $C_2$–$C_4$ paraffins by non-catalytic oxidative cracking of propane or propane-rich $C_2$–$C_4$ paraffins in the presence of steam, volatile sulfur compound and limited oxygen so that the endothermic thermal cracking and exothermic oxidative conversion reactions of propane, described later, occur simultaneously.

2. Another important object of this invention is to provide a non-catalytic process for the production of propylene and ethylene, with propylene/ethylene mole ratio of at least 0.15, from propane or propane-rich $C_2$–$C_4$ paraffins, which requires little (i.e. much smaller than that required for the thermal cracking process) or no external energy and also operates in a most energy efficient manner without any hazards (i.e. with a very safe process operation) through coupling of the exothermic oxidative hydrocarbon conversion reactions with the endothermic hydrocarbon cracking or pyrolysis reactions.

3. Yet another object of this invention is to be provide process for the production of propylene and ethylene, with propylene/ethylene mole ratio of at least 0.15, from propane or propane-rich $C_2$–$C_4$ paraffins by their simultaneous oxidative conversion and thermal cracking, which operates with high conversion, selectivity and productivity without deposition of coke on the reactor walls.

SUMMARY OF THE INVENTION

This invention provides a non-catalytic process for the production of propylene and ethylene, with propylene/ethylene mole ratio of at least 0.15, by oxidative cracking of propane or propane-rich $C_2$–$C_4$ paraffins with high conversion, selectivity and productivity, operating in most energy efficient and safe manner, in an empty tubular reactor. The process comprises of passing continuously a gaseous feed, comprising of propane or propane-rich $C_2$–$C_4$ paraffins, oxygen, steam, and volatile sulfur compound, preheated at 200°–550° C. through an empty tubular reactor at the temperature of 550°–900° C., pressure 0.5–5 atm, space velocity 500–50,000 $h^{-1}$ and mole ratios of $O_2$/hydrocarbon, steam/hydrocarbon and sulfur compound/hydrocarbon in the feed 0.01–1.0, 0.1–10 and $10^{-2}$–$10^{-6}$, respectively.

The main finding of this invention is that in the present process, the endothermic thermal cracking and exothermic oxidative hydrocarbon conversion reactions occur simultaneously and because of this there is a coupling of the exothermic and endothermic reactions and thereby the process operates in a most energy efficient manner and also without formation of hot spots in the reactor, making the process operation safe. Another important finding of this invention is that the present process requires a little or no external energy and it can be made thermoneutral or mildly exothermic or mildly endothermic by manipulating the process conditions. Yet another important finding of this invention is that the present process operates with high conversion, selectivity and productivity, producing propylene and ethylene with propylene/ethylene mole ratio of at least 0.15, and moreover there is no coke deposition on the reactor walls. Further one more important finding of this invention is that because of the addition of volatile sulfur compound in the feed, the propane conversion and/or selectivity for olefins is increased.

DETAILED DESCRIPTION OF THE INVENTION

Accordingly, this invention provides a process for the production of propylene and ethylene by non-catalytic oxidative cracking of propane or propane-rich-$C_2$-$C_4$ paraffins, which comprises:

a) mixing of oxygen or $O_2$-enriched air and propane or propane-rich $C_2$-$C_4$ paraffins at ambient temperature, b) mixing of a volatile sulfur compound with steam, c) admixing the mixture of steam and volatile sulfur compound and the mixture of oxygen or $O_2$-enriched air and propane or propane-rich $C_2$-$C_4$ paraffins, and preheating the resulting admixture to a temperature between about 200° C. to about 550° C., d) passing continuously the preheated admixture feed through an empty tubular reactor, while maintaining the mole ratio of oxygen to hydrocarbon, steam to hydrocarbon and volatile sulfur compound to hydrocarbon in said admixture feed between about 0.01 to about 1.0, between about 0.1 to about 10, and between about $10^{-2}$ to about $10^{-6}$, respectively, with a gas hourly space velocity of said admixture feed between about 500 h$^{-1}$ to about 50,000 h$^{-1}$ at a reaction temperature between about 620° C. to about 900° C. and a pressure between about 0.5 to about 5.0 atm, such that propylene to ethylene mole ratio in products is at least 0.15 and there is a coupling of exothermic hydrocarbon oxidative conversion and endothermic hydrocarbon cracking reactions due to the simultaneous occurrence of these exothermic and endothermic reactions, and e) cooling and separating the components of effluent product gases by known methods and, it required, recycling the unconverted reactants.

In the process of the present invention, the preferred reaction temperature is between about 635° C. and about 800° C.; the preferred pressure ranges from about 1 atm to about 3 atm; the preferred mole ratio of $O_2$ to hydrocarbon, steam to hydrocarbon and volatile sulfur compound to hydrocarbon in the feed ranges from about 0.05 to about 0.5, about 0.3 to about 3.0 and about $10^{-3}$ to about $10^{-5}$, respectively; and the preferred gas hourly space velocity of the feed ranges from about 1000 h$^{-1}$ to about 20,000 h$^{-1}$. The preferred volatile sulfur compound in the feed is thiophene.

In the process of the present invention, the products formed are propylene, ethylene, methane, ethane, hydrogen, carbon monoxide, carbon dioxide and water and $C_{4+}$ hydrocarbons. The gaseous product stream comprises of ethylene, propylene, $C_{4+}$ hydrocarbons, methane, ethane, $H_2$, CO, $CO_2$, $H_2O$ and unconverted propane and oxygen or air components.

The feed used in the process of the present invention comprises of propane or propane-rich $C_2$-$C_4$ paraffins, oxygen or $O_2$-enriched air, steam and volatile sulfur compound. The hydrocarbon components of the feed and oxygen are reactants but steam is a feed diluent and acts as an indirect reactant for the gasification of the carbon or coke formed in the process under oxygen deficient conditions or by thermal cracking or pyrolysis of hydrocarbons. The presence of steam in the feed has two beneficial effects: one, the formation of coke and tar-like product in the process are avoided and second, the severity of the exothermic hydrocarbon oxidation reactions is reduced due to the feed dilution. The steam in the product stream can be easily separated simply by its condensation. The oxygen in the feed plays following important roles in the process. Because of the presence of $O_2$ in the feed, not only the total conversion of propane but also its conversion purely by its thermal cracking is much higher than that observed in the absence of $O_2$. Further, because of the oxidation of coke precursors (i.e. hydrogen deficient or highly unsaturated hydrocarbon species formed in the conversion of the propane or propane-rich $C_2$-$C_4$ paraffins) by the oxygen, the coke formation in the process of this invention is avoided. The volatile sulfur compound in the feed plays two significant roles: (1) its passivates the inner walls surface of the tubular reactor by deactivating the coke forming sites present on the reactor inner walls through sulfidation and (2) its presence in the feed causes a significant increase in the conversion and/or selectivity for olefins. The preheating of the feed gases can be effected by exchanging heat between the hot reactor effluent product gas stream and the feed gases by known prior art methods.

Following non-catalytic exothermic and endothermic reactions occur in the process of present invention.

Exothermic reactions a) Oxidative dehydrogenation of propane or propane rich $C_2$-$C_4$ paraffins:

$$C_3H_8 + 0.5O_2 \rightarrow C_3H_6 + H_2O + 28.3 \text{ kcal.mol}^{-1} \text{ (at 700° C.)} \quad (1)$$

$$C_nH_{2n+2} + 0.5O_2 \rightarrow C_nH_{2n} + H_2O + \text{heat} \quad (2)$$

(when n=2–4)

b) Combustion of propane or propane rich $C_2$-$C_4$ paraffins, which are highly exothermic reactions:

$$C_3H_8 + 5O_2 \rightarrow 3CO_2 + 4H_2O + 489.0 \text{ kcal.mol}^{-1} \text{ (at 700° C.)} \quad (3)$$

$$C_3H_8 + 3.5O_2 \rightarrow 3CO + 4H_2O + 286.4 \text{ kcal.mol}^{-1} \text{ (at 700° C.)} \quad (4)$$

$$C_2\text{-}C_4 \text{ paraffins} + \text{oxygen} \rightarrow CO, CO_2 \text{ and } H_2O + \text{heat} \quad (5)$$

C) Oxidation of hydrogen to water, which is also highly exothermic:

$$H_2 + 0.5O_2 \rightarrow H_2O + 59.4 \text{ kcal.mol}^{-1} \quad (6)$$

Endothermic reactions

Thermal cracking or pyrolysis of propane or propane-rich $C_2$-$C_4$ paraffins:

$$C_3H_8 \rightarrow C_3H_6 + H_2 - 30.9 \text{ kcal.mol}^{-1} \text{ (at 700° C.)} \quad (7)$$

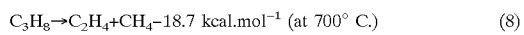

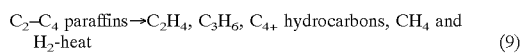

In the process of the present invention, since the above exothermic and endothermic reactions are occurring simultaneously, the heat produced in the exothermic reactions is used instantly for the endothermic reactions, thus making the process operation most energy efficient and safe. Since the thermal hydrocarbon cracking reactions have high activation energy, their reaction rate increases very fast with the increase in the temperature. The coupling of the exothermic and endothermic reactions, as described above, leads to an establishment of a sort of a buffer action for the reaction temperature in the process thus restricting the temperature rise and, therefore, an occurrence of run-away reaction condition during the operation of the process is totally eliminated. Because of the coupling of the exothermic and endothermic reactions occurring simultaneously, the process of this invention can be made mildly exothermic, thermoneutral or mildly endothermic by manipulating the process conditions.

The process can be operated in an empty non-adiabatic tubular reactor, containing single or multiple parallel coiled tubes, without any serious problems for removing heat from the reactor, when the process is mildly exothermic or providing energy to the reactor, when the process is mildly endothermic, thus requiring no or little (i.e. much smaller than that required for the thermal cracking process) external energy, respectively.

The present invention is described with respect to the following examples illustrating the process of this invention for the simultaneous exothermic oxidative conversion of propane or propane-rich $C_2$–$C_4$ paraffins and endothermic thermal cracking of propane or propane-rich $C_2$–$C_4$ paraffins in a most safe and energy efficient manner. These examples are provided for illustrative purposes only and are not to be construed as limitations on the invention.

Definition of terms used in the examples

Total conversion of reactant (%)=percent of the reactant converted to all the products. Conversion of a reactant to a particular product=percent of the reactant converted to the particular product.

Selectivity for a particular product (%)=100×[Conversion of reactant to the product (%)]/[Total conversion of reactant (%)].

Gas: hourly space velocity, GHSV=Volume of gaseous reactant mixture, measured at 0° C. and 1 atm pressure, passed through an unit volume of reactor per hour.

All the ratios of reactants or products are mole ratios.

The net heat of reactions, $\Delta H_r$, in the overall process is defined as follows:

Net heat of reactions, $\Delta H_r=[H_f]_{products}-[H_f]_{reactants}$.

Wherein, $[H_f]_{products}$ and $[H_f]_{reactants}$ are the heat of formation of products and reactants, respectively. The negative value of the net heat of reactions indicates that the overall process is exothermic and the positive value of the heat of reactions indicates that overall process is endothermic.

EXAMPLE 1

This example illustrates the process of this invention for the production of propylene and ethylene by non-catalytic oxidative cracking of propane in the presence of oxygen, steam and thiophene.

The process is carried out in a continuous flow empty tubular reactor having internal diameter of 7.0 mm and a volume of 5.2 cm³, by mixing oxygen with propane at room temperature, mixing thiophene vapors with steam, admixing the steam-thiophene mixture and oxygen-propane mixture, preheating the admixture and then passing continuously the preheated admixture through the reactor at the reaction conditions given below. The reactor was kept in an electrically heated tubular furnace. The reaction temperature was measured by a Chromel-Alumel thermocouple located axially in the center of the reactor. The reactor effluent gases were quenched and cooled at about 0° C. to condense the water from them, using a coiled condenser immersed in ice-water slurry, and then analyzed for the products and unconverted reactants by an on-line gas chromatograph.

Reaction conditions

| | |
|---|---|
| Feed | A mixture of propane, oxygen, steam and thiophene |
| Feed preheating temperature | 500° C. |
| $O_2$/propane mole ratio in feed | 0.25 |
| $H_2O$/hydrocarbon mole ratio in feed | 0.5 |
| Thiophene/propane mole ratio feed | $10^{-4}$ |
| Gas hourly space velocity (GHSV) | 3000 $h^{-1}$ |
| Pressure | 1.1 atm. |
| Reaction temperature | 800° C. |
| The results obtained at the above reaction conditions are as follows. | |
| No coke deposition is observed in the process. | |
| Conversion of propane (%) | 79.1 |
| Conversion of oxygen (%) | 93.5 |
| Selectivity (%) for | |
| Propylene | 21.8 |
| Ethylene | 42.4 |
| Methane | 19.6 |
| Ethane | 2.3 |
| $C_{4+}$ hydrocarbons | 5.6 |
| Carbon monoxide | 7.5 |
| Carbon dioxide | 0.8 |
| $C_3H_6/C_2H_4$ ratio in products | 0.34 |
| Net heat of reaction ($\Delta H_r$) (kcal.mol$^{-1}$) | −11.6 |

The net heat of reaction is small with —ve sign, indicating that the overall process is mildly exothermic. It also indicates that no external energy is required for the process.

EXAMPLES 2–27

These examples illustrate the process of the present invention for the production of propylene and ethylene by non-catalytic oxidative cracking of propane in the presence of oxygen, steam and different volatile sulfur compounds at different process conditions. The process is carried out in the reactor and by the procedure same as that described in Example 1. The process performance was evaluated at following process conditions.

| | |
|---|---|
| Feed | A mixtures of propane, oxygen, steam and volatile sulfur compound |
| Volatile sulfur compound | Thiophene, $CS_2$ or dimethyl sulfide (DMS) |
| Feed preheating temperature | 300° or 500° C. |
| $O_2$/propane mole ratio in feed | varied from 0.06 to 0.5 |
| Steam/propane mole ratio in feed | varied from 0.4 to 2.5 |
| Sulfur compound/propane mole ratio in feed | varied form $10^{-3}$ to $10^{-5}$ |
| Gas hourly space velocity (GHSV) | varied from 1170 to 7150 $h^{-1}$ |
| Pressure | 0.95–1.1 atm |
| Reaction temperature | varied from 600°–800° C. |

The results obtained at different process conditions are given in Tables 1–6. There was no coke deposition on the reactor walls.

This example also illustrates that the net heat of reactions in the process of this invention is quite small; it is with positive or negative sign, indicating that the process at the corresponding reaction conditions is mildly endothermic or mildly exothermic, respectively. This example also illustrates that the process of this invention occurs in a most energy efficient and safe manner and also the process can be made mildly exothermic, near thermoneutral or mildly endothermic by manipulating the process conditions, particularly the reaction temperature and the $O_2$/hydrocarbon mole ratio in the feed. This example further illustrates that for the process of present invention, either there is no requirement of external energy, particularly when the net heat of reaction, $\Delta H_r$ is negative (i.e. when the present process is mildly exothermic) or there is a requirement of much lower energy than that required for the thermal cracking of propane: $C_1H_x \rightarrow C_3H_6+H_2$, which is highly endothermic with a heat of radiation, $\Delta H_4=+39.93$ kcal.mol$^{-1}$ (at 727° C.). The external energy required in the process of process invention is much lower than that required for the propane thermal cracking process and hence there is a large energy saving.

EXAMPLE 28

This example illustrates that in the presence of limited $O_2$ in the feed of the process of present invention, not only the total conversion of propane but also the conversion of propane purely by its thermal cracking is much higher than that observed in the absence of $O_2$. The propane conversion reactions in the presence of $O_2$ and in the absence of $O_2$ were carried out in the reactor and by the procedure similar to that described in Example 1. Results showing the influence of the presence of $O_2$ in feed at different concentrations ($O_2/C_3H_8$ mole ratio=0–0.5) on the total conversion of propane and its conversion purely by thermal cracking at different temperatures (635°–800° C.) are presented in Table 7. Because of the presence of $O_2$, not only the total conversion of propane but also its conversion purely by thermal cracking is much higher that that observed in the absence of $O_2$. Both the total conversion of propane and its conversion by thermal cracking alone are increased markedly with increasing the concentration of $O_2$ relative to propane at all the temperatures.

TABLE 1

Results of the oxycracking of propane at different temperatures

|  | Example 2 | Example 3 | Example 4 | Example 5 |
|---|---|---|---|---|
| Process conditions |  |  |  |  |
| Reaction temp. (°C.) | 620 | 635 | 715 | 810 |
| $O_2/C_3H_8$ mole ratio | 0.5 | 0.5 | 0.5 | 0.5 |
| Steam/$C_3H_8$ mole ratio | 0.5 | 0.5 | 0.5 | 0.5 |
| Thiophene/$C_3H_8$ mole ratio | $10^{-4}$ | $10^{-4}$ | $10^{-4}$ | $10^{31\ 4}$ |
| GHSV (h$^{-1}$) | 3000 | 3000 | 3000 | 3000 |
| Pressure (atm) | 0.95 | 0.95 | 0.95 | 0.95 |
| Feed preheating temp. (°C.) | 500 | 500 | 500 | 500 |
| Conversion (%) of |  |  |  |  |
| Propane | 12.5 | 72.0 | 79.4 | 91.7 |
| Oxygen | 14.0 | 86.8 | 93.8 | 97.9 |
| Selectivity (%) for |  |  |  |  |
| Propylene | 58.3 | 26.2 | 20.1 | 13.8 |
| Ethylene | 28.9 | 38.2 | 40.5 | 44.0 |
| Methane | 4.2 | 14.3 | 16.6 | 19.7 |
| Ethane | 2.9 | 2.8 | 2.3 | 2.3 |
| $C_{4+}$hydrocarbons | 5.5 | 5.1 | 5.5 | 4.7 |
| Carbon monoxide | 2.0 | 12.6 | 13.6 | 14.5 |
| Carbon dioxide | 0.9 | 0.7 | 0.9 | 1.1 |

TABLE 1-continued

Results of the oxycracking of propane at different temperatures

|  | Example 2 | Example 3 | Example 4 | Example 5 |
|---|---|---|---|---|
| $C_3H_6C_2H_4$ mole ratio in products | 1.35 | 0.46 | 0.33 | 0.21 |
| Net heat of reaction $\Delta H_r$ (kcal.mol$^{-1}$) | −33.5 | −33.4 | −32.7 | −27.5 |

TABLE 2

Results of the oxycracking of propane at 800° C. for different $O_2/C_3H_8$ ratios

|  | Example 6 | Example 7 | Example 8 | Example 9 |
|---|---|---|---|---|
| Process conditions |  |  |  |  |
| Reaction temp. (°C.) | 800 | 800 | 800 | 800 |
| $O_2/C_3H_8$ mole ratio | 0.0 | 0.5 | 0.13 | 0.06 |
| Steam/$C_3H_8$ mole ratio | 0.5 | 0.5 | 0.5 | 0.5 |
| Thiophene/$C_3H_8$ mole ratio | $10^{-4}$ | $10^{-4}$ | $10^{-4}$ | $10^{-4}$ |
| GHSV (h$^{-1}$) | 3000 | 3000 | 3000 | 3000 |
| Pressure (atm) | 1.0 | 1.1 | 1.0 | 1.1 |
| Feed preheating temp. (°C.) | 500 | 500 | 500 | 500 |
| Conversion (%) of |  |  |  |  |
| Propane | 53.9 | 91.7 | 68.6 | 61.8 |
| Oxygen | — | 97.9 | 95.4 | 94.8 |
| Selectivity (%) for |  |  |  |  |
| Propylene | 29.3 | 13.3 | 25.4 | 27.2 |
| Ethylene | 41.9 | 44.0 | 42.2 | 42.1 |
| Methane | 20.4 | 19.7 | 19.7 | 19.7 |
| Ethane | 2.0 | 2.3 | 2.4 | 2.3 |
| $C_{4+}$hydrocarbons | 5.7 | 4.7 | 6.3 | 6.4 |
| Carbon monoxide | 0.5 | 14.5 | 3.4 | 1.8 |
| Carbon dioxide | 0.1 | 1.1 | 0.5 | 0.4 |
| $C_3H_6/C_2H_4$ mole ratio in products | 0.47 | 0.21 | 0.40 | 0.43 |
| Net heat of reaction $\Delta H_r$ (kcal.mol$^{-1}$) | — | −30.4 | +9.4 | +12.1 |

TABLE 3

Results of the oxycracking of propane at 635° C. for different $O_2/C_3H_8$ ratios

|  | Example 10 | Example 11 | Example 12 |
|---|---|---|---|
| Process conditions |  |  |  |
| Reaction temp. (°C.) | 635 | 635 | 635 |
| $O_2/C_3H_8$ mole ratio | 0.0 | 0.25 | 0.10 |
| Steam/$C_3H_8$ mole ratio | 0.5 | 0.5 | 0.5 |
| Thiophene/$C_3H_8$ mole ratio | $10^{-4}$ | $10^{-4}$ | $10^{-4}$ |
| QHSV (h$^{-1}$) | 3000 | 3000 | 3000 |
| Pressure (atm) | 1.0 | 1.0 | 1.0 |
| Feed preheating temp. (°C.) | 300 | 300 | 300 |
| Conversion (%) of |  |  |  |
| Propane | 0.8 | 47.8 | 22.8 |
| Oxygen | — | 91.9 | 94.1 |
| Selectivity (%) for |  |  |  |
| Propylene | 1.0 | 31.5 | 30.7 |
| Ethylene | 65.9 | 36.7 | 38.7 |
| Methane | 33.1 | 13.3 | 15.1 |
| Ethane | — | 2.3 | 2:2 |

TABLE 3-continued

Results of the oxycracking of propane at 635° C. for different $O_2/C_3H_8$ ratios

| | Example 10 | Example 11 | Example 12 |
|---|---|---|---|
| $C_{4+}$ hydrocarbons | — | 7.5 | 8.1 |
| Carbon monoxide | — | 8.3 | 4.6 |
| Carbon dioxide | — | 0.4 | 0.4 |
| $C_3H_6/C_2H_4$ mole ratio in products | 0.01 | 0.58 | 0.53 |

TABLE 4

Results of the oxycracking of propane at 635° C. for different steam/$C_3H_8$ ratios

| | Example 13 | Example 14 | Example 15 | Example 16 |
|---|---|---|---|---|
| Process conditions | | | | |
| Reaction temp. (° C.) | 635 | 635 | 635 | 635 |
| $O_2/C_3H_8$ mole ratio | 0.5 | 0.5 | 0.5 | 0.5 |
| Steam/$C_3H_8$ mole ratio | 0.4 | 1.13 | 1.6 | 2.5 |
| Thiophene/$C_3H_8$ mole ratio | $10^{-4}$ | $10^{-4}$ | $10^{-4}$ | $10^{-4}$ |
| GHSV ($h^{-1}$) | 3000 | 3000 | 3000 | 3000 |
| Pressure (atm) | 1.0 | 1.0 | 1.0 | 0.95 |
| Feed preheating temp. (°C.) | 500 | 500 | 500 | 500 |
| Conversion (%) of | | | | |
| Propane | 70.8 | 74.8 | 73.1 | 62.7 |
| Oxygen | 91.1 | 90.1 | 86.5 | 79.6 |
| Selectivity (%) for | | | | |
| Propylene | 24.9 | 25.4 | 28.1 | 28.9 |
| Ethylene | 38.3 | 38.0 | 35.5 | 36.4 |
| Methane | 14.0 | 14.0 | 12.3 | 11.7 |
| Ethane | 2.5 | 2.6 | 2.4 | 2.3 |
| $C_{4+}$ hydrocarbons | 7.4 | 10.2 | 9.1 | 5.2 |
| Carbon monoxide | 12.3 | 13.0 | 12.1 | 14.7 |
| Carbon dioxide | 0.6 | 0.8 | 0.5 | 0.7 |
| $C_3H_6/C_2H_4$ mole ratio in products | 0.44 | 0.45 | 0.53 | 0.53 |

TABLE 5

Results of the oxycracking of propane at 635° C. for different space velocities

| Example | 17 | 18 | 19 | 20 | 21 |
|---|---|---|---|---|---|
| Process conditions | | | | | |
| Reaction temp. (°C.) | 635 | 635 | 635 | 635 | 635 |
| $O_2/C_3H_8$ mole ratio | 0.5 | 0.5 | 0.5 | 0.5 | 0.5 |
| Steam/$C_3H_8$ mole ratio | 0.5 | 0.5 | 0.5 | 0.5 | 0.5 |
| Thiophene/$C_3H_8$ mole ratio | $10^{-4}$ | $10^{-4}$ | $10^{-4}$ | $10^{-4}$ | $10^{-4}$ |
| GHSV ($h^{-1}$) | 1170 | 2355 | 3530 | 4730 | 7150 |
| Pressure (atm) | 0.95 | 1.0 | 1.05 | 1.0 | 1.1 |
| Feed preheating temp. (°C.) | 500 | 500 | 500 | 500 | 500 |
| Conversion (%) of | | | | | |
| Propane | 88.1 | 88.2 | 88.5 | 75.5 | 23.7 |
| Oxygen | 98.7 | 98.6 | 96.1 | 84.5 | 36.4 |
| Selectivity (%) for | | | | | |
| Propylene | 27.1 | 22.9 | 21.3 | 27.1 | 35.9 |
| Ethylene | 38.0 | 41.2 | 41.1 | 41.2 | 40.1 |
| Methane | 16.1 | 14.4 | 15.4 | 14.2 | 11.9 |
| Ethane | 2.9 | 3.9 | 2.6 | 1.6 | 1.6 |
| $C_{4+}$ hydrocarbons | 3.5 | 3.2 | 3.1 | 2.3 | 4.8 |
| Carbon monoxide | 10.8 | 12.6 | 13.8 | 10.1 | 2.2 |
| Carbon dioxide | 1.7 | 1.8 | 2.8 | 1.6 | 1.4 |
| $C_3H_6/C_2H_4$ mole ratio in products | 0.48 | 0.37 | 0.35 | 0.44 | 0.60 |

TABLE 6

Results of the oxycracking of propane at 635° C. for different sulfur compound additives in the feed

| Example | 22 | 23 | 24 | 25 | 26 | 27 |
|---|---|---|---|---|---|---|
| Process conditions | | | | | | |
| Reaction temp. (°C.) | 635 | 635 | 635 | 635 | 635 | 635 |
| $O_2/C_3H_8$ mole ratio | 0.5 | 0.5 | 0.5 | 0.5 | 0.5 | 0.5 |
| Steam/$C_3H_8$ mole ratio | 0.5 | 0.5 | 0.5 | 0.5 | 0.5 | 0.5 |
| Sulfur compound additive | Thiophene | Thiophene | Thiophene | Thiophene | $CS_2$ | DMS |
| Sulfur compound/$C_3H_8$ mole ratio | 0.0 | $1 \times 10^{-5}$ | $1 \times 10^{-4}$ | $1 \times 10^{-4}$ | $1 \times 10^{-4}$ | $1 \times 10^{-4}$ |
| GHSV ($h^{-1}$) | 3000 | 3000 | 3000 | 3000 | 3000 | 3000 |
| Pressure (atm) | 1.0 | 1.0 | 1.0 | 1.0 | 1.0 | i.0 |
| Feed preheating temp. (°C.) | 500 | 500 | 500 | 500 | 500 | 500 |
| Conversion (%) of | | | | | | |
| Propane | 70.8 | 76.2 | 77.1 | 75.7 | 7101 | 78.6 |
| Oxygen | 91.1 | 91.4 | 91.9 | 91.0 | 92.3 | 91.1 |
| Selectivity (%) for | | | | | | |
| Propylene | 24.9 | 23.8 | 26.2 | 23.6 | 25.2 | 21.6 |
| Ethylene | 38.3 | 39.4 | 38.2 | 38.2 | 40.1 | 44.0 |
| Methane | 14.0 | 14.6 | 14.0 | 14.5 | 14.0 | 14.5 |
| Ethane | 2.5 | 2.8 | 2.9 | 2.7 | 2.9 | 2.5 |
| $C_{4+}$ hydrocarbons | 7.4 | 6.3 | 5.6 | 6.5 | 6.7 | 6.8 |
| Carbon monoxide | 12.3 | 12.5 | 12.4 | 13.3 | 12.5 | 13.8 |
| Carbon dioxide | 0.6 | 0.6 | 0.7 | 0.6 | 0.6 | 0.7 |
| $C_3H_6/C_2H_4$ mole ratio in products | 0.44 | 0.40 | 0.46 | 0.41 | 0.42 | 0.33 |

TABLE 7

Total conversion of propane and its conversion purely by thermal cracking at different temperatures and concentrations of $O_2$ (relative to propane) in the feed. Reaction conditions: steam/$C_3H_8$ and thiophene/$C_3H_8$ ratios in feed = 0.5 and $1 \times 10^{-4}$, respectively and GHSV = 3000 $h^{-1}$ and feed preheating temperature = 500° C.

| | $O_2/C_3H_8$ | Propane conversion (%) | |
|---|---|---|---|
| Temp. (°C.) | ratio | Total | Thermal cracking |
| 635 | 0.00 | 0.8 | 0.8 |

TABLE 7-continued

Total conversion of propane and its conversion purely by thermal cracking at different temperatures and concentrations of $O_2$ (relative to propane) in the feed. Reaction conditions: steam/$C_3H_8$ and thiophene/$C_3H_8$ ratios in feed = 0.5 and $1 \times 10^{-4}$, respectively and GHSV = 3000 h$^{-1}$ and feed preheating temperature = 500° C.

| Temp. (°C.) | $O_2/C_3H_8$ ratio | Propane conversion (%) | |
|---|---|---|---|
| | | Total | Thermal cracking |
| | 0.06 | 15.1 | 7.0 |
| | 0.13 | 23.4 | 6.3 |
| | 0.25 | 47.0 | 27.4 |
| | 0.50 | 72.0 | 42.4 |
| 660 | 0.00 | 1.6 | 1.6 |
| | 0.50 | 74.7 | 49.0 |
| 715 | 0.00 | 7.5 | 7.5 |
| | 0.50 | 74.7 | 56.6 |
| 800 | 0.00 | 53.9 | 53.9 |
| | 0.06 | 61.8 | 59.0 |
| | 0.13 | 68.6 | 62.2 |
| | 0.25 | 79.2 | 72.6 |
| | 0.50 | 91.7 | 77.4 |

The main advantages of this invention or major improvement achieved by this invention over the earlier processes for the production of propylene from propane or $C_2$–$C_4$ paraffins are as follows 1. In the process of this invention, because of the simultaneous occurrence of the endothermic hydrocarbon cracking reactions and the exothermic oxidative hydocarbon conversion reactions, the heat produced in the exothermic reactions is used instantly in the endothermic reactions and there is a coupling of the exothermic reactions with the endothermic ones. This has imparted following outstanding features to the process of the present invention:
    a) The process is operated in a most energy efficient manner with large energy saving, achieving high conversion of paraffins with high selectivity for propylene and ethylene, with propylene/ethylene mole ratio of at least 0.15, and also the process is operated at higher space velocity at lower contact time, thus increasing the productivity or space-time-yield of propylene and other olefins.
    b) The process is operated in a very safe manner with no possibility of reaction run-away conditions.
    c) The process can be made mildly exothermic, near thermoneutral or mildly endothermic by manipulating the process conditions.
    d) The process can be operated in a non-adiabatic empty tubular-reactor without any serious problems for removing heat from the reactor, when the process is mildly exothermic or for providing energy to the reactor, when the process if mildly endothermic, thus requiring no or much smaller external energy than that required for the thermal cracking process.
    e) Because of the presence of oxygen, not only the rate of total conversion of propane but also the rate of thermal cracking of propane, which is occurring simultaneously with the oxidative conversion of propane is increased, hence the process is operated at low contact time and thereby the productivity of propylene and ethylene in the process of this invention is higher than that in the earlier thermal cracking process operating in the absence of oxygen and also propylene and ethylene are produced with propylene/ethylene mole ratio of at least 0.15.

2. Because of the presence of oxygen in the feed, there is no coke deposition on the reactor walls in the process of this invention. Whereas, in the earlier thermal cracking process, there is an extensive coke deposition in the pyrolysis reactor tubes, causing increase in pressure drop across the reactor and ultimately process breakdown for the coke removal. Also because of coke deposition, the life of the reactor tubes in the thermal cracking process is low. These limitations of the earlier thermal cracking process are also overcome in the process of present invention.

3. The process of this invention has also number of advantages over the earlier process based on the catalytic oxidative dehydrogenation of propane to propylene.
    a) The process of this invention does not involve a use of catalyst and therefore there are no problems of catalyst deactivation due to sintering or loss of active components or coke deposition. The process operating cost is also reduced, as no catalyst is required.
    b) The process of this invention can be made thermoneutral, mildly exothermic or mildly endothermic by controlling the simultaneously occurring exothermic oxidative conversion and endothermic thermal cracking reactions; hence the process occur in a most energy efficient and safe manner and the operation of process is simple. Whereas the catalytic dehydrogenation is highly exothermic and hence it is a hazardous process; it is not safe to operate.
    c) The reactor design, process operation control for the catalytic oxidative dehydrogenation process are much more complicated because of its hazardous nature and catalyst deactivation and heat and mass transfer problems in the catalytic process, as compared to the non-catalytic process of this invention.

We claim:

1. A process for the production of propylene and ethylene by non-catalytic oxidative cracking of propane or propane-rich $C_2$–$C_4$ paraffins, which comprises:
    a) mixing oxygen or $O_2$-enriched air and propane-rich $C_2$–$C_4$ paraffins at ambient temperature,
    b) mixing a volatile sulfur compound with steam,
    c) admixing the mixture of steam and volatile sulfur compound and the mixture of oxygen or $O_2$-enriched air and propane or propane-rich $C_2$–$C_4$ paraffins and preheating the resulting admixture to a temperature between about 200° C. to about 550° C.,
    d) passing continuously the preheated admixture feed through an empty tubular reactor, while maintaining the mole ratio of oxygen to hydrocarbon between about 0.01 to about 1.0, steam to hydrocarbon mole ratio between about 0.1 to about 10 and volatile sulfur compound to hydrocarbon mole ratio between about $10^{-2}$ to about $10^{-6}$ in said admixture feed, with a gas hourly space velocity of said admixture feed between about 500 h$^{-1}$ to about 50,000 h$^{-1}$ at a reaction temperature between about 620° C. to about 900° C. and a pressure between about 0.5 to about 5.0 atm, such that propylene/ethylene mole ratio in the products is at least 0.15 and there is a coupling of exothermic hydrocarbon oxidative conversion and endothermic hydrocarbon cracking reactions due to the simultaneous occurrence of these exothermic and endothermic reactions, and
    e) cooling and separating the components of effluent product gases and, if required, recycling the unconverted reactants.

2. A process as claimed in claim 1 wherein the reaction temperature is maintained between about 635° C. and about 800° C.

3. A process as claimed in claim 1 wherein the pressure employed ranges from about 1.0 atm to about 3.0 atm.

4. A process as claimed in claim 1 wherein the mole ratio of $O_2$ to hydrocarbon, steam to hydrocarbon and volatile sulfur compound to hydrocarbon in feed ranges from about 0.05 to about 0.5, from about 0.3 to about 3.0 and from about $10^{-3}$ to about $10^{-5}$, respectively.

5. A process as claimed in claim 1 wherein the gas hourly space velocity of feed ranges from about 1000 $h^{-1}$ to about 20,000 $h^{-1}$.

6. A process as claimed in claim 1 wherein the volatile sulfur compound in the feed is thiophene.

* * * * *